United States Patent [19]

Boyd et al.

[11] Patent Number: 5,041,388
[45] Date of Patent: Aug. 20, 1991

[54] C-TERMINAL PEPTIDE SEQUENCING, ACTIVATED SUPPORT AND REAGENT SYSTEM THEREFOR, AND METHOD OF PRODUCING THE ACTIVATED SUPPORT

[75] Inventors: Victoria L. Boyd, San Carlos; David H. Hawke, Hayward, both of Calif.

[73] Assignee: Applied Biosystems, Inc., Foster City, Calif.

[21] Appl. No.: 547,088

[22] Filed: Jun. 29, 1990

Related U.S. Application Data

[63] Continuation-in-part of Ser. No. 454,666, Dec. 21, 1989.

[51] Int. Cl.$^5$ .......................... C07K 1/10; G01N 33/68
[52] U.S. Cl. ........................................ 436/89; 422/61; 436/178; 525/326.2; 525/327.7; 525/328.3; 525/333.5; 525/333.6; 525/393; 530/345; 530/408
[58] Field of Search .................... 436/89, 178; 422/61; 525/333.5, 333.6, 326.2, 328.3, 393, 327.7; 530/345, 408

[56] References Cited

U.S. PATENT DOCUMENTS 4,935,494 6/1990 Miller ............................... 436/89 X

FOREIGN PATENT DOCUMENTS

0217634A2 4/1987 European Pat. Off. .
1250863 10/1989 Japan ..................................... 436/89

OTHER PUBLICATIONS

Rangarajan, M., in "Protein/Peptide Sequence Analysis: Current Methodologies" (1988), Capter 7, pp. 135-144, A. S. Bhown, Ed.

Miller, C. G. et al., "Studies on the Use of Silyl Compounds for Protein Carboxy-Terminal Sequence Analysis" (1989), Techniques in Protein Chemistry, pp. 67-78, T. E. Hugh, Ed., Academic Press.

Tarr, G. E., Methods in Protein Sequence Analysis (1988), Section 4.1: "The Long Search for a Viable Method of C-Terminal Sequencing", pp. 129-151, B.

Wittman-Leibold, Ed., Proceedings of the 7th International Conf., Berlin.

Hawke, D. H. et al., Microsequence Analysis of Peptides and Proteins: Trimethylsilylisothiocyanate as a Reagent for COOH-Terminal Sequence Analysis (1987), Analytical Biochem. 166, pp. 298-307.

Parham, M. E. et al., Carboxy-Terminal Sequential Degradation, (1978), Bioch. Biophys. Res. Comm., vol. 80, pp. 1-6.

Kenner, G. W. et al., in Peptides IV, 136, "Selective Removal of the C-Terminal Residue as a Thiohydantoin" (1953), J. Chem. Soc.

Stark, G. R., in "Methods in Enzymology", (1972), vol. 25, p. 369, Academic Press.

Miller, M. J . et al., The Chemistry of the Method for the Determination of Carboxyl-Terminal Residues in Peptides (1977), Org Chem., vol. 42, pp. 1750-1761.

Meuth, J. L., et al., Stepwise Sequence Determination from the Carboxy-Terminal Residue of Peptides (1982), Biochemistry, vol. 16, pp. 3750-3757.

Parham, M. E., et al., A New Method of Determination of the Carboxy-Terminus of Peptides (1978), Biochem. Biophys. Res. Comm., vol. 80, pp. 7-13.

Dewar, M. J. S., et al., Ground States of Molecules. 38., The MNDO Method. Approximations and Parameters (1977), J. Am. Chem. Soc. 99:15, pp. 4899-4907.

Primary Examiner—Robert J. Hill, Jr.
Attorney, Agent, or Firm—Joseph A. Smith; Peter J. Dehlinger

[57] ABSTRACT

A method of C-terminal peptide sequencing. The peptide is reacted with an activated support derivatized with a mixed anhydride of isothiocyanic acid and carboxylic or carbonic acid, under basic conditions. The peptidyl thiohydantoin which forms is separated from the solid support and further reacted with a cleaving agent carried on a second solid support, to release a free C-terminal amino acyl thiohydantoin from the peptide. The free thiohydantoin is analyzed to determine the C-terminal peptide residue. The residual peptide can be recycled through the supports for successive C-terminal residue determinations.

22 Claims, 8 Drawing Sheets

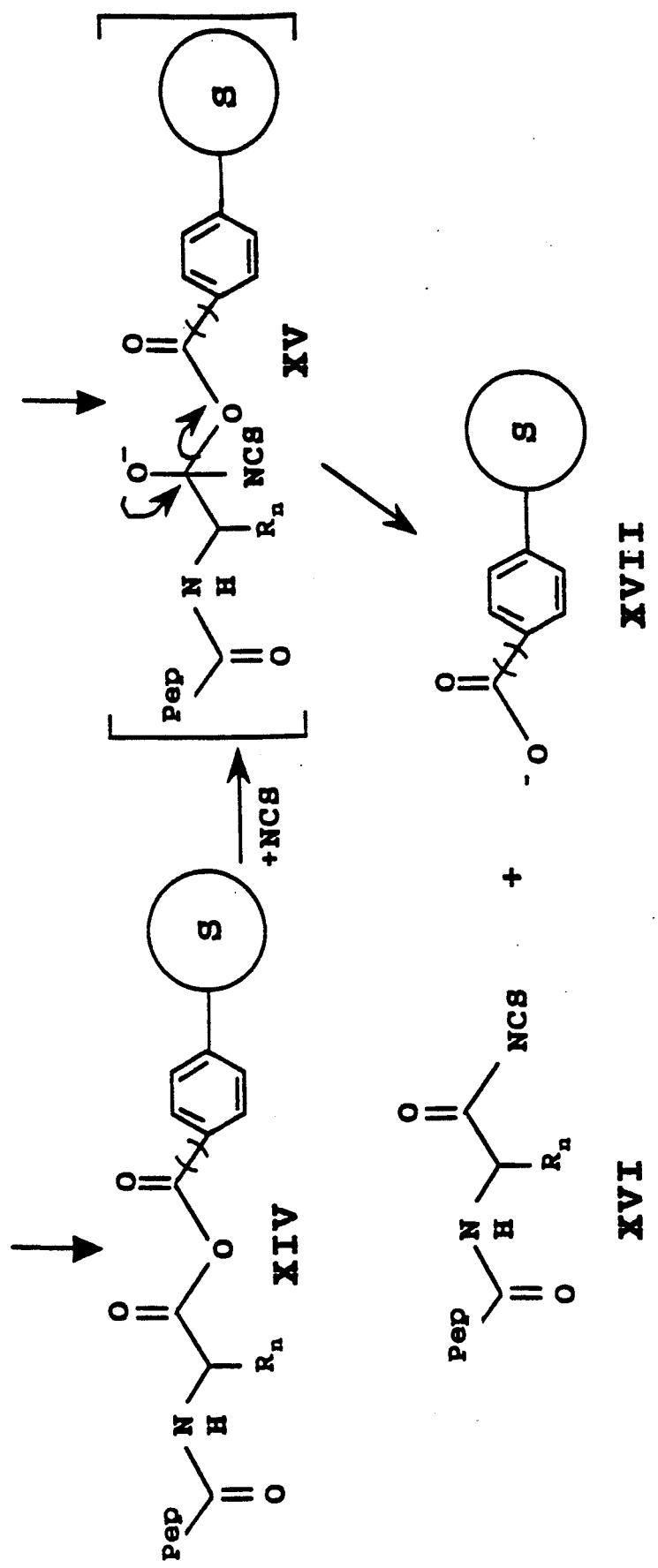
Fig. 5A (con't)

C-TERMINAL PEPTIDE SEQUENCING, ACTIVATED SUPPORT AND REAGENT SYSTEM THEREFOR, AND METHOD OF PRODUCING THE ACTIVATED SUPPORT

This application is a continuation-in-part of copending patent application for "Method of C-Terminal Peptide Sequencing," Ser. No. 454,666, filed Dec. 21, 1989 pending.

FIELD OF THE INVENTION

The present invention relates to a method for determining the C-terminal amino acid of a peptide, and to a solid phase system for use in the method.

REFERENCES

Carey and Sundberg, Advanced Organic Chemistry, p. 30.
    Dewar, M. J. S., JACS 99(15):4899 (1977).
    Edman, P., Acta Chem Scand, 4:277 (1950).
    Green, T., Protecting Groups in Organic Synthesis, Academic Press
    Hawke, D. H., et al, Anal Biochem, 166:298 (1987).
    Kenner, G. W., et al, J Chem Soc, 673 (1953).
    Meuth, J. L., Biochemistry, 16:3750 (1982).
    Miller, M. J., et al, J Org Chem, 42:1750 (1977).
    Miller, C. G., et al, in "Techniques in Protein Chemistry (Hugh, T. E., ed.), Academic Press, pp. 67–78 (1989).
    Parham, M. E., et al, Biochem Biophys Res Commun, 80:7 (1978).
    Stark, G. R., in Methods in Enzymology (Hirs, C. H. W., et al, eds.), Vol 25, p 369 Academic Press (1972).
    Woodward, R. B., et al., Tetrahedron, Supplement #7, 415-440 (1966).
    Woodward, R. B., et al., J Am Chem Soc, 83:1007-1009 (1961).
    Yamashita, S., Biochimica et Biophysica Acta, 229:301-209 (1971).

BACKGROUND OF THE INVENTION

Determining the amino acid sequence, i.e., primary structure, of a peptide is central to understanding the structure of the peptide, as well as to manipulating the peptide to achieve desired properties in a modified or altered form. In addition, the amino acid sequence of a peptide is useful in a variety of recombinant DNA procedures for identifying the gene coding sequence of the peptide, for producing the peptide recombinantly, and/or for producing site-specific modifications of the peptide.

Methods for use in N-terminal sequencing are well known (e.g., Edman). Despite the relative ease and reliability of N-terminal sequencing methods, it is often desired to obtain C-terminal amino acid sequence information which may be inaccessible or only obtained with difficulty by this method. Information about the carboxy terminal sequence may be useful for certain types of recombinant DNA procedures, particularly since the C-terminal end of the coding region of a protein corresponds to the end closest to a poly A tail, which is likely to be present in CDNA clones.

Three general approaches have been proposed for C-terminal peptide sequencing: enzymatic, physical, and chemical. These methods and their inherent limitations have been summarized in the above-cited parent application. Briefly, neither enzymatic nor physical determinations have proven satisfactory to date. In view of this, considerable effort has been invested in developing chemical methods for determining C-terminal amino acids residues, and for C-terminal sequencing. An inherent difficulty in C-terminal sequencing is the relatively poor reactivity of the carboxyl group, in contrast to the relative ease of addition at the N-terminal amino group.

Of the reaction methods which have been proposed for C-terminal sequencing, three have received special attention.

The first method involves generating a carboxyamido derivative at the C-terminal end of the peptide, followed by reaction with bis(I,I-trifluoroacetoxy)iodobenzene, to form a derivative which rearranges and hydrolyses to a shortened carboxyamidopeptide and the aldehyde derivative of the C-terminal amino acid (Parham). The method has been successfully carried out only to 3–6 cycles before the reaction halts. In a second, related approach, the carboxy terminus is reacted with pivaloylhydroxamate to effect a Lossen rearrangement. One limitation of the method is that the chemistry does not degrade aspartic and glutamic acid residues (Miller, 1977).

The most widely studied of the C-terminal chemistries is the thiohydantoin (TH) reaction. In one general method for carrying out the TH method, the carboxyl group is activated with an anhydride, such as acetic anhydride, in the presence of an isothiocyanate (ITC) salt or acid, to form a C-terminal peptidyl-TH via a C-terminal ITC intermediate (Stark, 1972). The peptidyl-TH can be cleaved to produce a shortened peptide and a C-terminal amino acid TH, which can be identified, e.g., by high pressure liquid chromatography (HPLC). The coupling conditions in this method typically require about 90 minutes at a 60° C.–70° C. (Meuth), and often lead to degradation of some of the amino acid side chains in the peptide. Further, the anhydride reagent is relatively unstable, and therefore presents storage problems.

A C-terminal TH sequencing method which can be carried out under milder conditions has been described by one of the inventors and co-workers (Hawke). Using trimethylsilyl isothiocyanate (TMSITC) as the reagent, TH formation was achieved by activation of the peptide with acetic anhydride for 15 min at 50° C., followed by reaction with TMS-ITC for an additional 30 min at 50° C. The method suffers from the disadvantage, noted above, of peptide exposure to a highly reactive anhydride activating agent. In addition, and like the related TH-generating methods described above, the TH-amino acid reaction products are racemized, and thus the method cannot be used to distinguish D- and L-form amino acids.

The C-terminal sequencing methods involving TH formation just described commonly lead to racemized products. A modification of the C-terminal reaction employing phosphoryl isothiocyanatidate reagent has been proposed (Kenner). Although TH was produced, the reaction was too slow to be very useful. Miller et al have proposed a related method, but using a mercaptobenzothiazole derivative. The rationale for using this compound is that cyclization could occur with concomitant opening of the thiazole ring.

In co-pending parent application for "Method of C-Terminal Peptide Sequencing" there is disclosed an improved C-terminal sequencing method which (a) is relatively rapid, (b) can be carried out under mild reaction conditions, and (c) under acidic peptidyl TH cleavage conditions maintains the stereochemistry of the C-terminal amino acid. In the disclosed method, the peptide is reacted with a mixed anhydride of isothiocyanic acid and a carboxylic, carbonic, or sulfonic acid, preferably a carboxylic acid, under basic conditions, to produce a C-terminal peptidyl TH. Subsequent hydrolysis of the reaction product releases the amino acid TH, which can then be identified as an amino acid TH adduct. The residual peptide can be recycled through the method steps, for successive C-terminal sequence determination.

One feature of the just-described method is that the C-terminal amino acid TH must be purified from solution-phase reactants and byproducts, such as mixed anhydride reactant, the organic acid byproduct of thiohydantoin formation, the cleavage reagent and its byproducts.

SUMMARY OF THE INVENTION

It is one object of the present invention to provide a C-terminal sequencing method which provides the advantages of the method disclosed in the above-cited application, in that the method (a) is relatively rapid, (b) can be carried out under mild reaction conditions, and (c) may maintain the stereochemistry of the C-terminal amino acid. At the same time, the present method can be carried out under conditions in which the reactants and byproducts of the sequencing reaction are sequestered on a solid support.

It is a more general object of the invention to provide a method and immobilized reagent for producing an amino acid TH.

It is still another object of the invention to provide a system for C-terminal sequencing which employs the support reagent.

In the method of the invention for producing an amino acid TH, an N-protected amino acid, which may include the C-terminal amino acid of a peptide, is contacted with a solid support derivatized with a mixed anhydride of isothiocyanic acid and carboxylic or carbonic acid, under basic conditions in which the carboxyl group of the amino acid is deprotonated. The amino acid TH formed in solution is separated from the solid support, such as by eluting the product from the support.

The acyl ITC support preferably has the form:
solid support

where A is an alkyl, alkoxy, aryl, or aryloxy group attached to the solid support. The solid support may be derivatized by activation with Woodwards Reagent K or an anhydride reagent, followed in both cases by reaction with an ITC, or by reaction with a solution-phase acyl ITC of the type disclosed in the above-cited parent application.

For use in C-terminal peptide sequencing, where the reaction with the solid support produces a C-terminal peptidyl TH, the method further includes cleaving the C-terminal amino acid TH from the residual peptide and identifying the cleaved amino acid TH, such as by HPLC. In a preferred embodiment, the peptidyl TH is contacted with a second solid support having a cleaving agent effective to cleave the peptidyl TH from the residual peptide. The peptide is preferably retained on the solid support, either by ion-exchange binding, or by covalent linkage which forms during the cleavage reaction. After elution of the amino acid TH in the solution phase, the residual peptide may be released and recycled for further sequence determination.

In another aspect, the invention includes an activated support composed of a solid support derivatized with a mixed anhydride of isothiocyanic acid and carboxylic or carbonic acid, and preferably having the form:
solid support

where A is an alkyl, alkoxy, aryl, or aryloxy group attached to the solid support.

Also forming part of the invention is a system for solution-phase C-terminal sequencing. The system includes an activated support of the type just described, and preferably a second solid support capable of (i) cleaving a peptidyl TH to release the amino acid TH, and (ii) binding the residual peptide to the support. The residual peptide can be selectively released from the support after the amino acid TH has been recovered. The system may include a series of such supports, for successive C-terminal peptide determinations.

These and other objects and features of the invention will become more fully apparent when the following detailed description of the invention is read in conjunction with the accompanying drawings.

DETAILED DESCRIPTION OF THE INVENTION

A. Solid-Phase ITC Reagent

The method of the invention employs an acyl ITC solid-phase (immobilized) reagent which is derivatized with an acyl ITC, i.e., a mixed anhydride of a carboxylic or carbonic acid, and isothiocyanic acid. The reagent has the form:

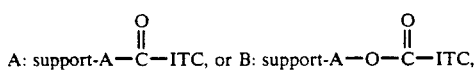

where A is an alkyl, alkoxy, aryl, or aryloxy group and ITC is isothiocyanate, also designated N=C=S or NCS in the figures. The alkyl group may be selected from the group of alkyl and cycloalkyl compounds, such as methyl, ethyl propyl, t-butyl, and related carbon-containing compounds linked to the acyl carbon through a carbon-carbon linkage. The aryl group may be a benzene, substituted benzene, or related aromatic or heteroaromatic compound linked to the acyl carbon through an aryl ring carbon atom. The group of compounds indicated at A are also referred to herein as mixed anhydrides of ITC and carboxylic acids, since hydrolysis at the CO-N bond yields a carboxylic acid an ITC. The group of compounds indicated at B are likewise referred to herein as mixed anhydrides of isothiocyanic acid and carbonic acids, since hydrolytic cleavage of the compounds produce a carbonic acid ester and NCS.

The solid support may be particle beads, or a membrane support, or the like, derivatized with surface chemical groups by which the support can be functionalized to contain acyl ITC. A variety of bead or membrane support materials, such as glass or a number of polymer materials, such as nylon, polystyrene, polyethylene, Teflon$^{TM}$ (polytetrafluorethylene) having reactive chemical groups, such as amine, carboxyl, and hydroxyl groups which can be converted by a variety of known methods to the desired reactive ITCs are commercially available.

Figure 1:
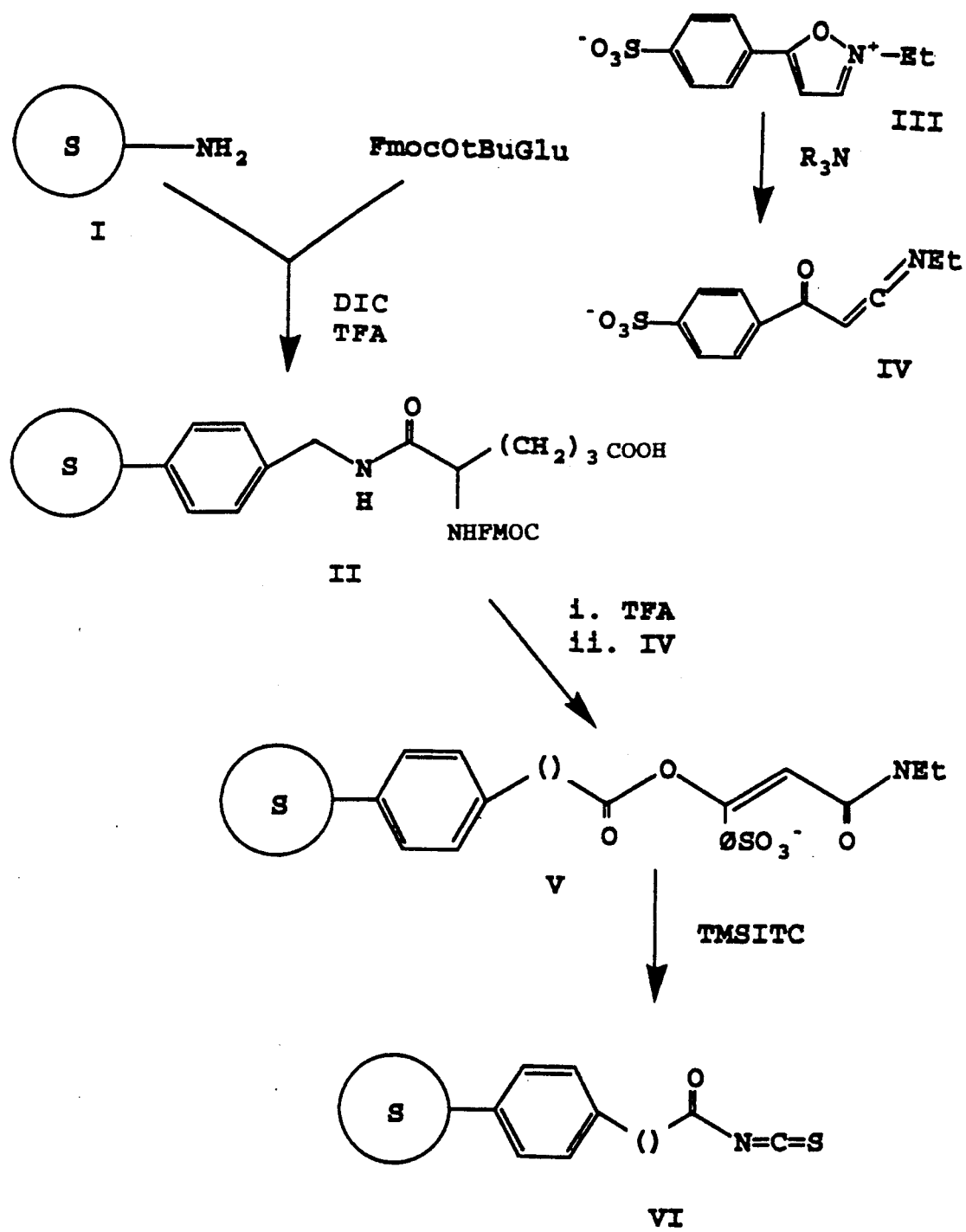
FIG. 1 shows the reaction steps for forming an activated solid support using Woodwards Reagent K to activate carboxyl groups on the support.

FIG. 1 illustrates the steps in the formation of an activated solid support derivatized with acyl ITC groups. The solid support (I) is a particle bead or the like, indicated at S, having surface amine groups. The beads are first derivatized to contain carboxylic acid surface groups by reaction of the beads with a side chain-protected dicarboxylic acid such as FMOC-Glu-OtBu, and a carbodiimide reagent in a suitable solvent, to couple the dicarboxylic acid derivative to the amino surface groups through an amide linkage. The protected carboxylated support is shown at (II) in FIG. 1. Reaction conditions are detailed in Example 1A. The functional group is deprotected, e.g. with TFA.

It will be appreciated that the support could have been similarly prepared using other routes to generate a carboxylated support.

The support (II) is activated by reaction with an isoxazolium salt, such as Woodwards Reagent K (Woodward) (III). In the presence of a suitable base, such as a trialkyl amine, the isoxazolium salt forms a ketenimine (IV) which can react with the free carboxyl group of the support, to form an activated enol ester (V). The activated ester is reacted with an ITC compound, such as trimethylsilyl ITC (TMSITC), to form the desired activated acyl ITC solid support (VI). Specific reaction conditions are given in Example 1B. Preferred ITC compounds trialkysilyl-ITC compounds, such as TMS-ITC, or pyridinium thiocyanate. The parentheses in structures V and VI represent the glutanic acid link in the support shown in structure II.

Figure 2:
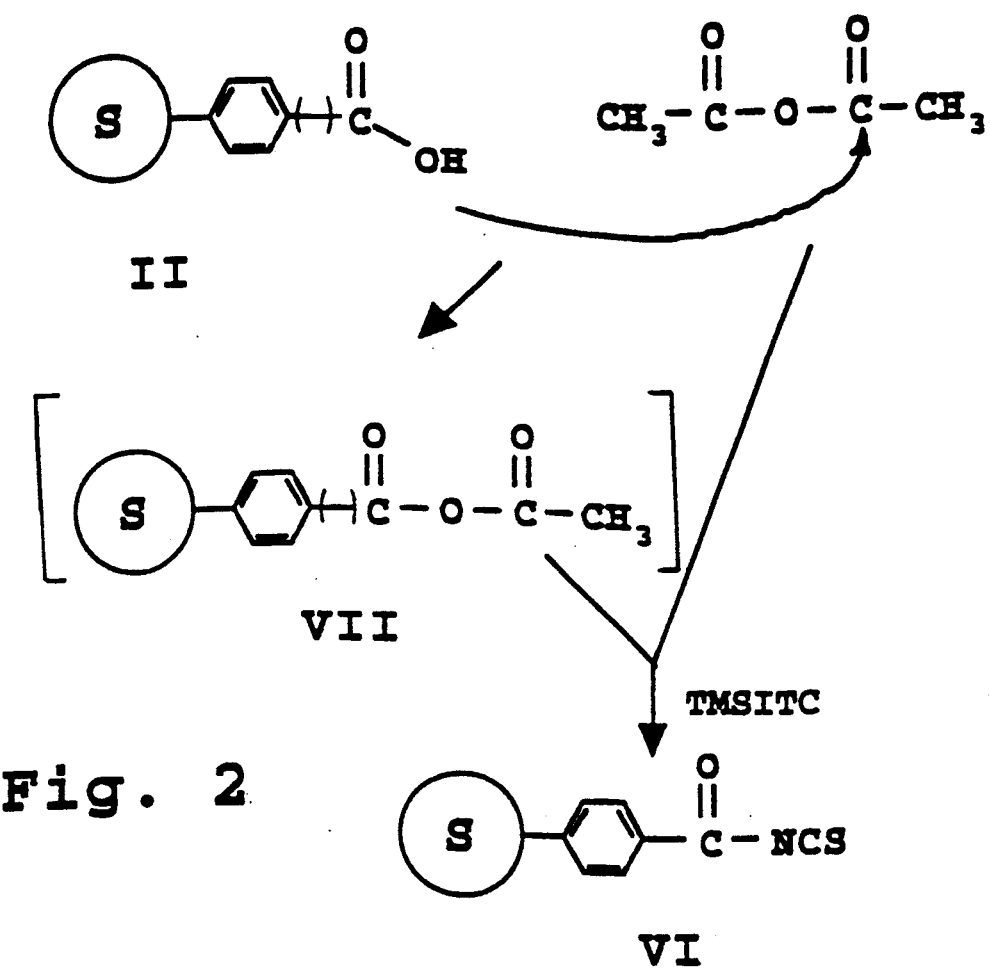
FIG. 2 shows the reaction steps for forming a solid support using an acid anhydride to activate the carboxyl groups on the support.

FIG. 2 illustrates a second general method for forming a solid support activated with benzoyl ITC. Here support (II) is reacted with an anhydride, such as acetic anhydride, under anhydrous conditions, to form a presumed activated anhydride support (VII). Further reaction with an ITC compound, such as TMSITC, yields the desired benzoyl ITC activated support (VI). Details of the reaction are provided in Example 2.

Figure 3:
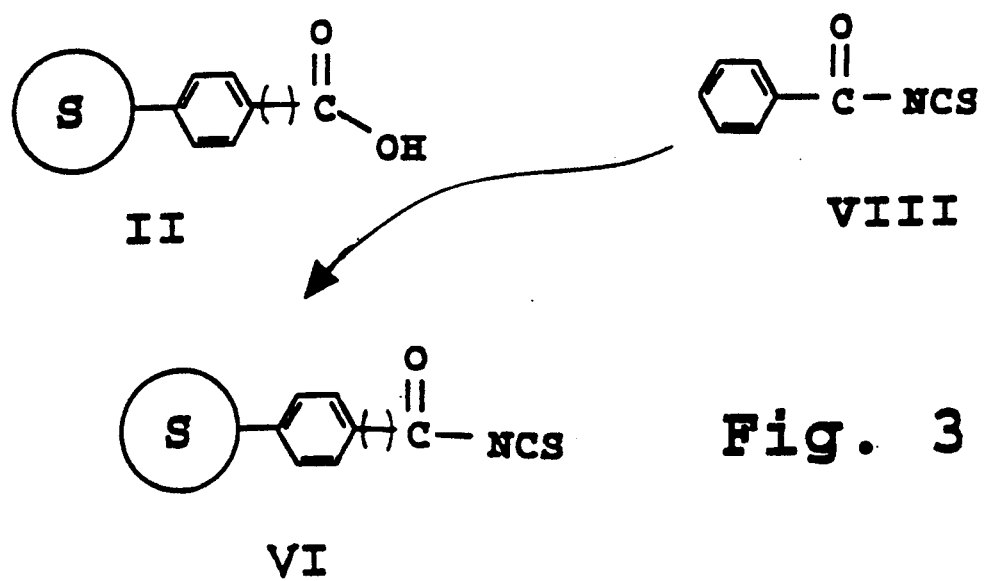
FIG. 3 shows the reaction steps for forming an activated solid support using a solution-phase acyl-ITC to activate carboxyl groups on the support.

A third method for forming an activated mixed anhydride ITC solid support is illustrated in FIG. 3. In this method, a solution-phase acyl ITC compound, such as benzoyl ITC (VII), reacts directly with the carboxyl groups on the solid support to form the desired activated acyl ITC support. Details of the reaction are given in Example 3.

Solution-phase ITC compounds may be obtained commercially or prepared as described in the above-cited parent application. In one method of preparing acyl ITC, an ITC salt is added in a dry, inert solvent containing a base to an acid chloride.

Figure 4:
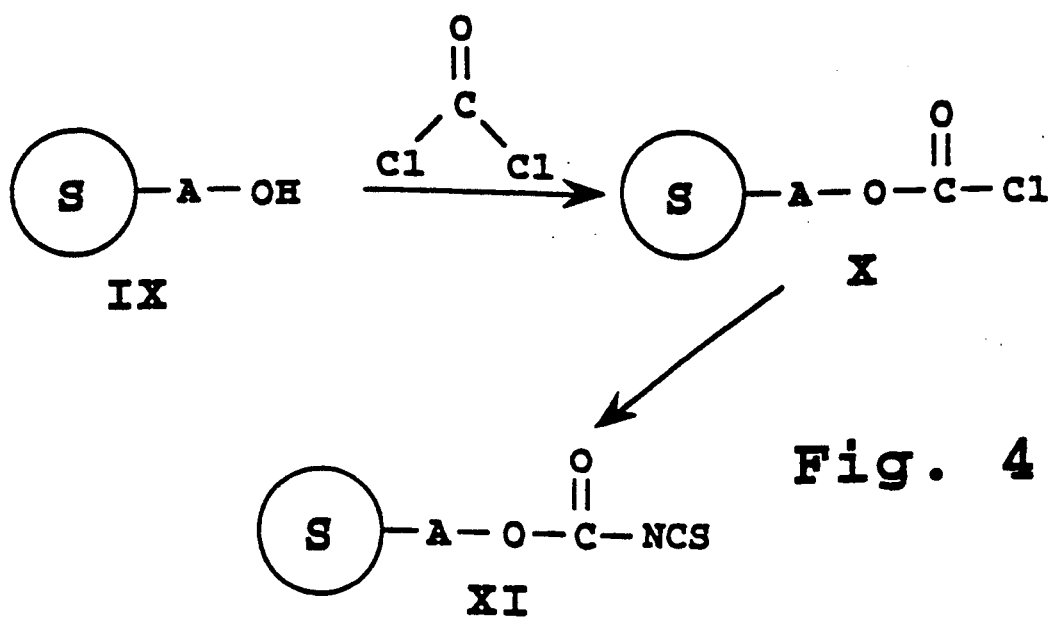
FIG. 4 shows the reaction steps for forming an activated solid support derivatized with a mixed anhydride of carbonic acid and ITC.

FIG. 4 illustrates a method of forming an activated solid support derivatized with a mixed anhydride of a carbonic acid and ITC. The solid support (IX) used in the method is derivatized with alkyl or aryl (A) alcohol groups, according to known methods. This support is activated with a phosgene equivalent, such as triphosgene, to form the corresponding activated carbonate derivative (XI). Further reaction with an ITC, such as TMSITC, gives the desired activated support (XII). The reaction conditions given in Example 4 are illustrative.

The activated support may be stored in stable form dried or in an aprotic, non-nucleophilic solvent, such as benzene or toluene until used.

B. Peptidyl-TH Formation

In practicing the method of the invention, a peptide whose C-terminal amino acid is to be identified is reacted with the acyl ITC reagent under basic conditions, preferably in the presence of pyridine, in which the C-terminal acid group of the amino acid is deprotonated. The C-terminal amino acid is converted to a C-terminal amino acid TH which is linked to the next-in C-terminal amino acid in the peptide through a ring-nitrogen amide bond.

The amino groups of a peptide are first protected with acetylation or formation of BOC (t-butyloxycarbonyl) or FMOC (fluourenylmethoxycarboxyl) derivatives, according to standard methods (Green). The N-protected peptide is dissolved in a suitable solvent, such 10% pyridine in acetonitrile, at a final peptide concentration typically between .1 and 10 μg/ml. The peptide solution is then added to the mixed-anhydride solid-phase reagent, preferably in molar excess of the activated mixed anhydride group. Typically, about per 100 μL of the peptide solution is added to 10 μg of the solid-phase reagent.

The TH-forming reaction is preferably carried out at 50° C.-60° C., for about 10-60 minutes, preferably at about 50° C. for 15-30 minutes, to minimize reaction of the ITC reagent with non-carboxyl groups in the peptide. Typical reaction conditions are given in Example 5.

Figure 5A:
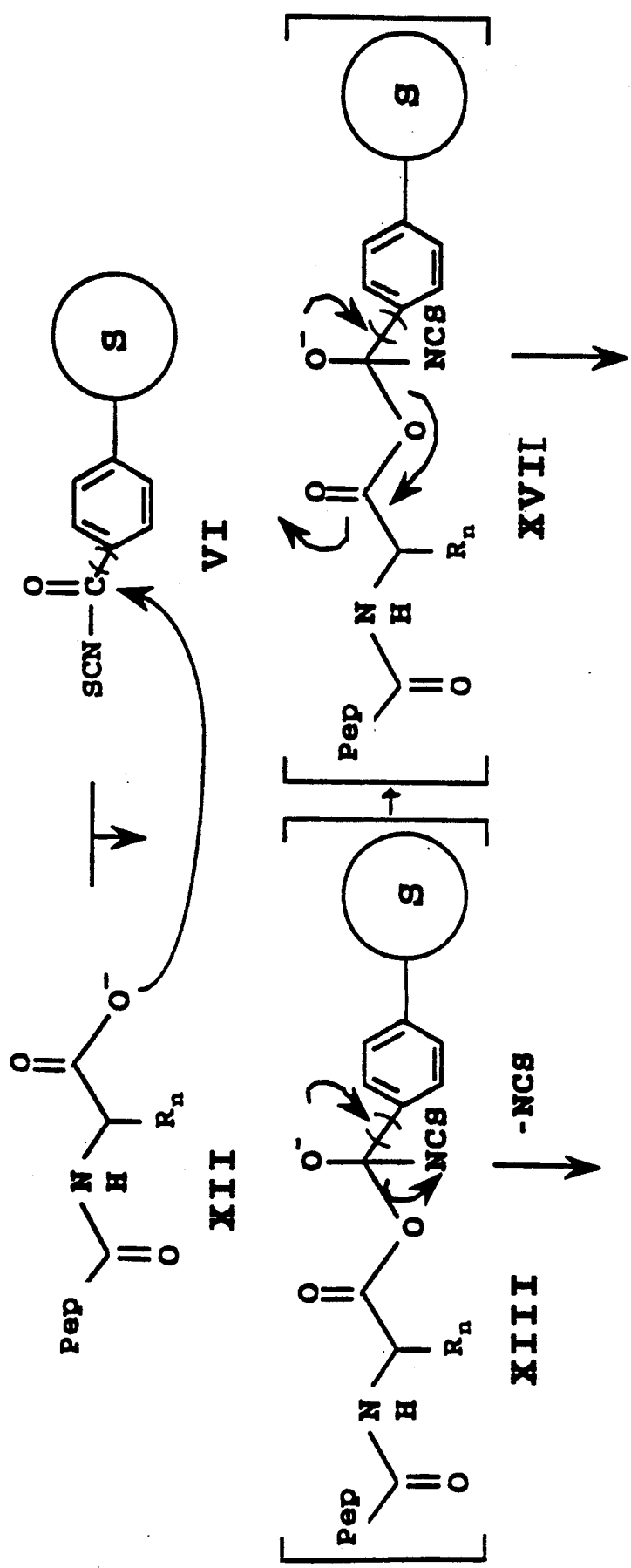
FIGS. 5A and 5B show reaction schemes for formation of a peptidyl TH by peptide reaction with an activated acyl ITC support, in accordance with the invention (5A), and the cyclization of peptidyl-ITC to form peptidyl TH (5B)

FIG. 5 shows reaction mechanisms for the formation of a peptidyl TH by reaction with the activated support of the invention. In the mechanism shown at the left in FIG. 5A, the peptide (XII) reacts at the carbonyl carbon of the mixed anhydride reagent (VI), through the intermediate XIII, to form the peptidyl acyl-ITC shown at XIV in the figure. The anhydride reacts with a free thiocyanate ion produced in the reaction, to form a peptidyl ITC (XVI). In this proposed mechanism, the mixed anhydride reagent functions both as an activating reagent, to form a reactive peptidyl anhydride, and as a source of thiocyanate ions for reaction with the anhydride.

An alternative reaction mechanism is shown at the right in FIG. 5A. Here the thiocyanate group in the tetrahedral intermediate XVII in the figure migrates in a possibly converted fashion to the peptide carbonyl carbon, forming the tetrahedral intermediate XV which rapidly collapses to form the corresponding peptide ITC compound (XVI).

With continued reference to FIG. 5A, there are two possible electrophilic sites of reaction of the peptidyl deprotonated (nucleophilic) oxygen atom. The first site, and the one shown in the FIG. 5A reaction scheme, is the carbonyl carbon. The second site is the thiocarbonyl (thiocyanate) carbon. As reported in the earlier-filed parent application, reaction studies involving solution-phase mixed anhydrides indicate that the alkyl and aryl carbonyl groups (the mixed anhydrides of isothiocyanic acid and carboxylic acids) give the highest percentage of the desired carbonsite reaction product under the specified reaction conditions (in the presence of pyridine), and, correspondingly, the lowest percentage of reaction products resulting from nucleophilic attack at the thiocyanate carbon. The sulfonic acid mixed anhydride reagent gives the lowest percentage of the desired product.

Figure 6:
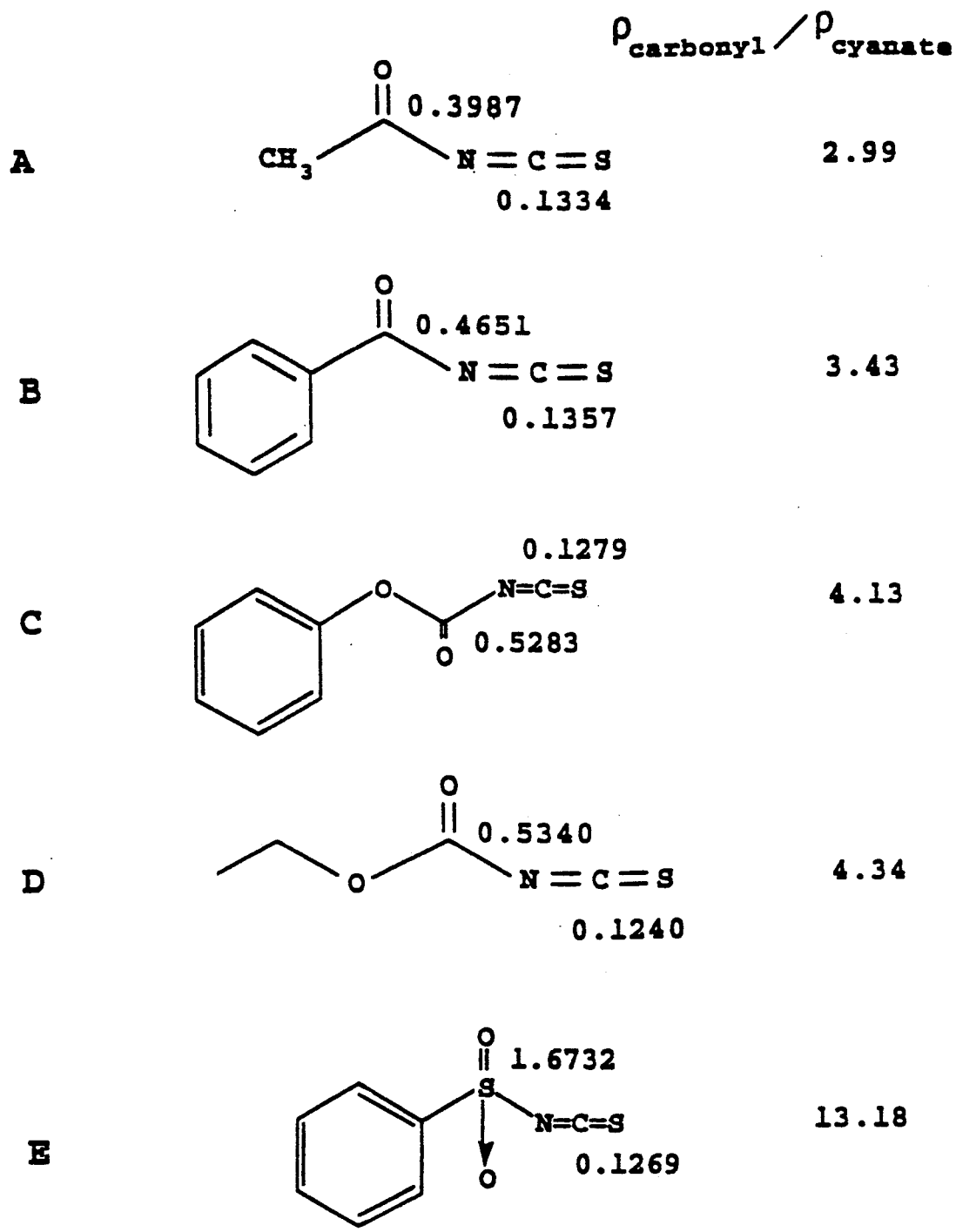
FIG. 6 shows a variety of mixed anhydride ITC compounds, with the calculated atomic charge on the carbonyl carbon, sulfonyl sulfur atom, and ITC carbon atom indicated for each compound.

Molecular orbital calculations were carried out on the mixed anhydrides shown in FIG. 6, which includes alkyl (A) and aryl (B) mixed anhydrides of carboxylic acid, alkyl (C) and aryl (D) anhydrides of carbonic acid, and an aryl mixed anhydride of sulfonic acid (E). The calculations were performed by the Modified Neglect of Diatomic Orbitals (MNDO) procedure (Dewar), using the MOPAC program available form the Quantum Chemistry Program Exchange (Bloomington, IN). The partial charges calculated for the carbonyl and cyanate carbon atoms by the program are shown for the five molecules in the figure, as well as the ratio of carbonyl/cyanate carbon-atom charge, arranged in ascending order. The calculations may be used to examine the likely effect of aryl or alkyl substitutions on the peptidyl TH reaction. For example, calculations of the charge ratios of benzoyl ITC's indicate that strongly electron withdrawing substituents, such as F or NO, on the phenyl ring have little effect on the relative partial charge ratio, indicating little effect on the ratio of the reaction products.

The yields of mixed products observed for the five compounds shown in FIG. 6, and the charge ratios calculated for the compounds, indicate that the cyanate carbon is activated by high partial charge at the carbonyl carbon (or sulfonyl sulfur), and thus becomes a more probable site for nucleophilic attack. This is analogous to the observed reactivity of an alpha-beta unsaturated ketone, where a greater partial charge at the ketone carbon leads to enhanced reactivity of the beta carbon toward nucleophilic attack (Carey, Sundberg). Although this reaction scheme might predict that the mixed anhydride of an alkyl carboxylic acid (e.g., compound A), would give best product yields, the higher reactivity of the alkyl carbonyl carbon may also make the mixed anhydride more susceptible to hydrolysis, and this may explain the somewhat greater yields of desired peptidyl-ITC product observed with the aryl carboxylic acid mixed anhydride.

Figure 5B:
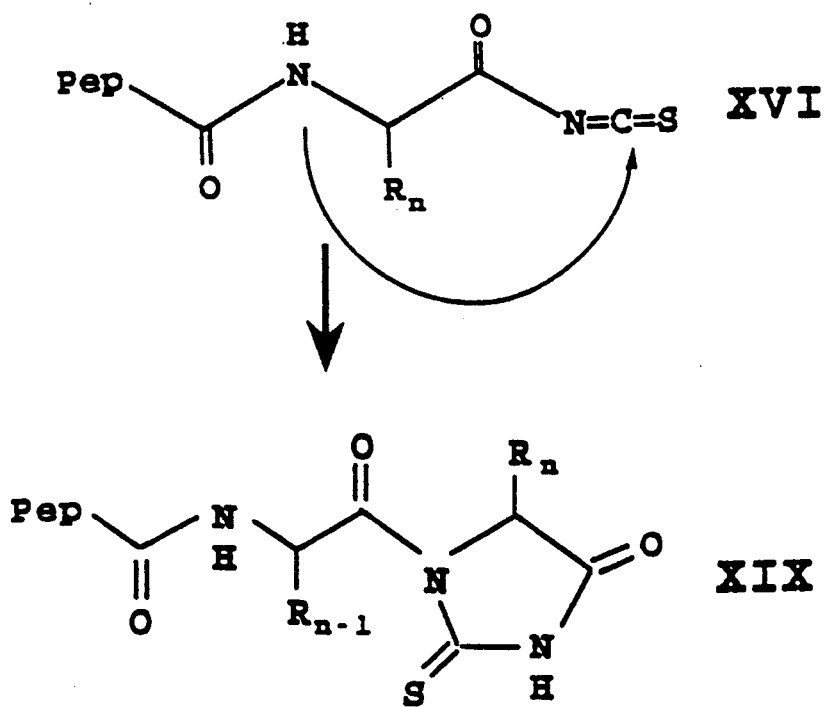

The cyclization of the peptidyl ITC compound to form the desired peptidyl TH is shown in FIG. 5B, and presumably involves a electrophilic attack by the thiocyanate carbon on the amide nitrogen in the peptide ITC compound, with rapid cyclization to form the peptidyl TH shown at XIX in the figure. The cyclization reaction may be catalyzed by pyridine, suggesting that pyridine may be reacting with the thiocyanate moiety to enhance the reactivity of the reactive carbon center, as has been proposed (Miller, 1989).

Following the reaction of the peptide with the activated solid support, the resultant peptidyl TH is separated from the solid support, by washing or eluting the reaction mixture from the solid support. According to an important feature of the invention, the only reaction components for converting a protected peptide to a peptidylTH are carried on the solid support, and no reaction products are released by the support in forming the peptidyl TH. That is, the peptidyl TH separated from the solid support is free of activating reagents or reagent byproducts of the TH-formation reaction.

Also as seen at the bottom of FIG. 5A, the reaction regenerates the original (pre-activated) acid form of the solid support. The solid support can be reactivated by any of the activation reactions described above with respect to FIGS. 1-3.

In another aspect, the invention includes a method of producing an amino acid TH from an N-protected amino acid. The method is similar to that described above, substituting an N-protected amino acid for an N-protected peptide. Following formation of an amino acyl-ITC and cyclization to form the corresponding amino acid TH, the product is separated from the solid support, yielding a protected amino acid TH free of reactants and side reaction products. The isolated amino acid TH can be deprotected, e.g., under acid or base conditions, according to known methods.

C. Formation and Identification of Amino Acid TH

This section describes the final steps of the method of the invention, which include (a) treating the peptidyl TH under cleavage conditions effective to cleave the amide linkage joining the TH to the residual peptide, and (b) isolating and identifying the isolated amino acid TH.

A variety of cleavage reaction conditions are known. Hydrolytic cleavage with 12 N HCl, dilute alkali (Kenner), or saturated aqueous triethylamine have been reported. These cleavage reactions are reported to yield up to 70% percent cleavage, but the extreme pH conditions can lead to ring opening and/or damage to internal peptide side chains. Cleavage by treatment with acetohydroxamate in pyridine at pH 8.0 has also been reported (Meuth). The method affords recovery yields of up to 60%-80% of the C-terminal TH (Miller, 1989). Another method involves treatment with primary or secondary amines in acetonitrile.

Figure 7:
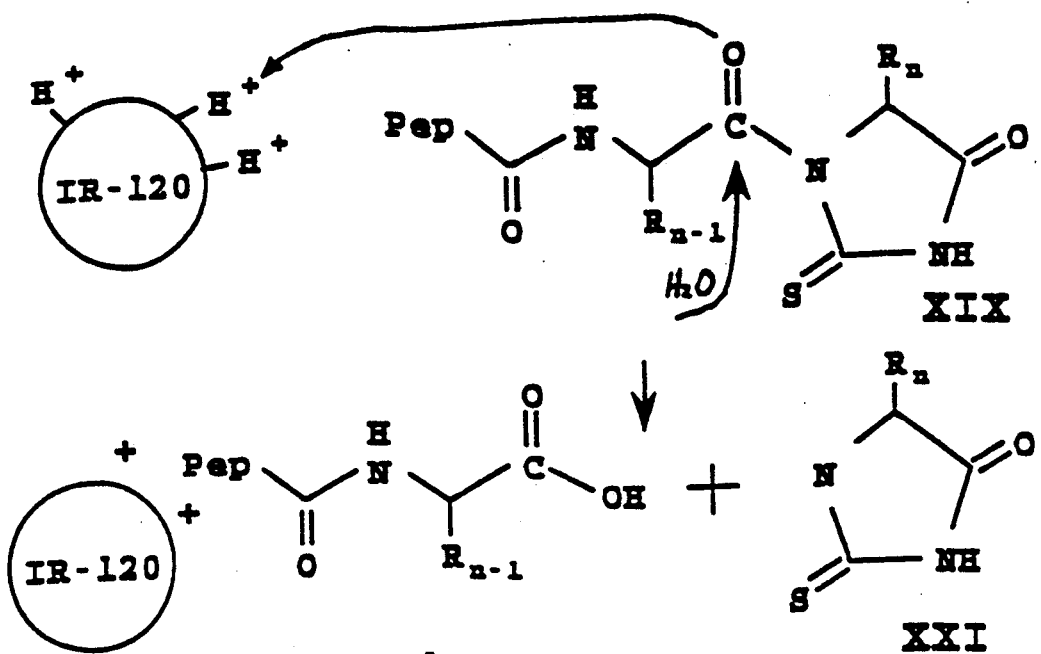
FIG. 7 illustrates the steps in cleaving a peptidyl TH by a cation-exchange resin, and binding of the residual peptide to the resin support.

In a preferred method, the cleavage reaction is carried out by contacting the peptidyl TH in a suitable solvent with a solid-phase cleaving reagent. One solid-phase cleavage reagent which has been reported (Yamashita) is a cation-exchange resin Amberlite® IR-120 (protonated form), available from Aldrich, (Milwaukee, WI). As illustrated in FIG. 7, the resin promotes the acid-catalyzed hydrolysis of the peptidyl TH, yielding the desired amino acid TH (XXI) and residual peptide (XX). Typically, the peptidyl TH sample is added to the resin (about 2 mequiv H+ available per gram resin), and the mixture is incubated for 2-6 hours at room temperature. The peptide solution is prepared typically by removing the solvent used in peptidyl TH formation by vacuum, and redissolving the peptidyl TH in aqueous medium.

The residual peptide may be bound to the cation-exchange resin, allowing the free amino acid TH to be separated from the residual peptide, by washing the resin under low ionic strength conditions. With the residual peptide bound to the support, the free amino acid TH can be obtained by washing or elution in substantially purified form. The residual peptide may be released subsequently by eluting at elevated ionic strength or pH.

The residual peptide and amino acid TH formed as above may alternatively be separated, if necessary, by passage through a anion exchange resin, or by chromatography, for example, with by HPLC or molecular sieve chromatography.

In a second general embodiment, the cleavage reagent is derivatized with a chemical group capable of reacting with the peptidyl TH, to release free amino acid TH and link the residual peptide covalently. The free amino acid TH can then be isolated in substantially purified form by washing or elution, and the residual peptide can be released by hydrolytic cleavage of the peptide from the support.

Figure 8:
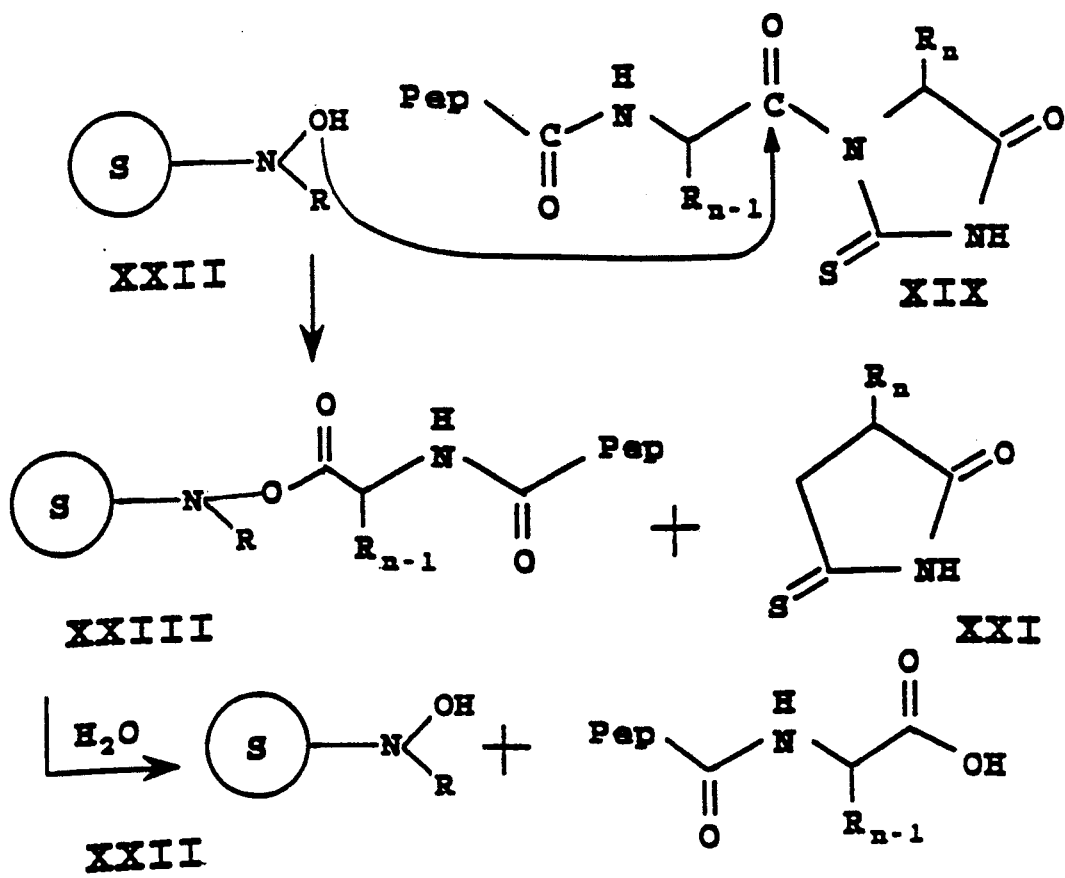
FIG. 8 illustrates the steps in cleaving a peptidyl TH by a solid support derivatized with hydroxylamine groups, and subsequent hydrolytic release of the residual peptide from the resin/support.

One exemplary solid-phase cleavage reagent is the N-alkyl derivatized solid support (XXII) shown in FIG. 8. The R group in the figure is preferably a methyl or other small alkyl group. As shown, hydrolytic cleavage of the peptidyl TH by the hydroxylamime group on the solid support forms an 0-hydroxamate ester attachment of the residual peptide to the support, with the release of free amino acid TH. The reaction is preferably carried out in an aprotic solvent, such as MeCN, in the presence of an organic base, such as thilthylamine (TEA).

After recovery of the amino acid TH, the residual peptide can be hydrolytically cleaved from the support by contact with acidified aqueous medium, as indicated at the bottom in FIG. 8. Thus the method allows for isolation of amino acid TH and residual peptide separately, each in substantially purified form free of reactants and side products. The hydrolytic cleavage regenerates the hydroxylamine support.

The released amino acid TH compound may be identified by known chromatographic methods, such as high pressure liquid chromatography (HPLC), according to standard procedures. Compound identification can be made conveniently by comparing the run times in the columns with the run times of known reference amino acid TH's, prepared according to standard methods, or by the method of preparing an amino acid TH described above. Alternatively, the released and isolated amino acid TH can be identified by other available methods, such as mass spectrometry or NMR.

More generally, the invention contemplates hydrolytic cleavage of a peptidyl-TH reagent with a secondary hydroylamine having the general formula:

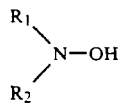

where $R_1$, $R_2$ are each alkyl or aryl groups, preferably alkyl, where one of the N substituents may be attached to a solid support. In this more general embodiment, a peptidyl-TH, either in solution or immobilized on a solid support, is reacted in water or in an organic solvent, such as acetonitrile, with the secondary hydroxyl amine which itself may be in solution (e.g., where the peptidyl-TH is immobilized), or immobilized (where the peptidyl-TH is in solution).

Preferred secondary hydroxylamines are dialkyhydroxylamines, such as dimethy- or diethyl-hydroxylamine, which are commercially available. Aryl hydroxyamines are also suitable, but may interfere with amino acid TH detection. Aryl hydroxylamines may also rearrange under acidic conditions to undesired amino phenols. $R_1$, $R_2$, may also be acyl groups, although these compounds may be overly susceptible to hydrolysis under aqueous conditions.

D. C-Terminal Solution-Phase Sequencing

This section describes the application of the above method to a C-terminal solution-phase sequencing method which is suitable for automated or semi-automated operation. As used herein, "solution phase sequencing" refers to sequencing reactions in which the peptide is retained in solution, and recycled successively through solid-phase reagents. This is in contrast to solid-phase sequencing, where the peptide is immobilized on a solid support, and is repeatedly exposed to solution-phase C-terminal residue activating and cleavage reagents.

Figure 9:
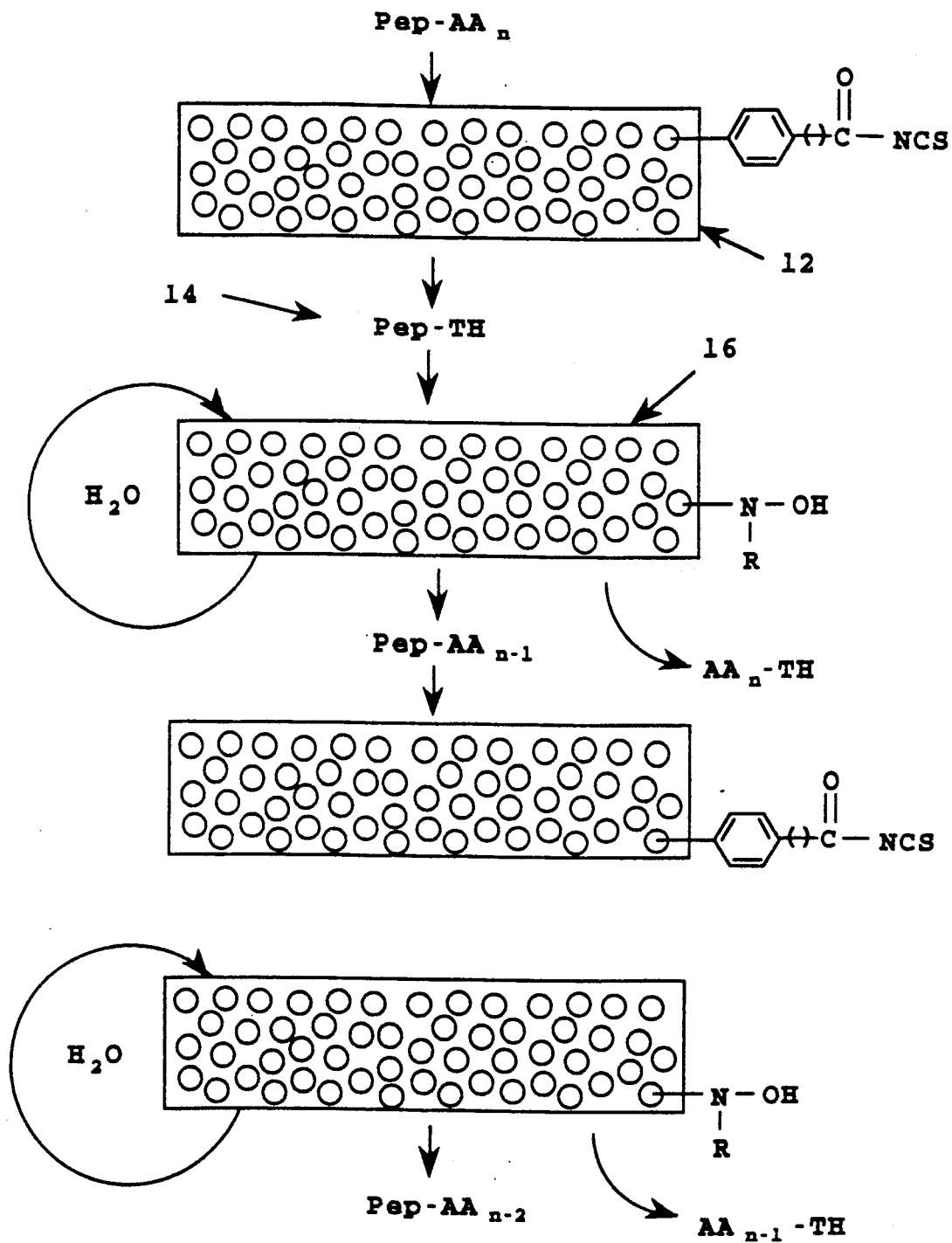
FIG. 9 illustrates the steps in a C-terminal sequencing operation in accordance with the invention.

FIG. 9 illustrates the general sequencing scheme as it is applied to a peptide Pep-$AA_n$, i.e., a peptide having n residues and a C-terminal residue $AA_n$. Initially, the peptide is dissolved in a suitable non-nucleophilic solvent such as pyridine in acetonitrile, and added to an activated solid-support resin contained in a packed column indicated at 12. Column 12 is preferably part of a two-stage cartridge 14 which also includes a column 16 containing a solid-support cleavage reagent.

After reacting the peptide with the activated support, the reaction solution, which contains peptidyl TH is eluted from column 12 into column 16. Optionally, the two columns may be separated by an intermediate chamber (not shown), where the column 12 solvent may be removed by vacuum and replaced by a second solvent before sample introduction into column 16. In a preferred embodiment, the solid-support reagent is the type illustrated in FIG. 8. This support has the advantages that (a) the cleavage reaction can be carried out in the same non-aqueous solvent or solvent mixture used in the column-12 reaction, and (b) the binding to and release from the support of the residual peptide to the support is covalent, and therefore not dependent on the charge characteristics of the peptide.

The cleavage reaction is carried out under conditions as described above, after which the C-terminal amino acid TH ($AA_n$-TH) is eluted from the column and identified, e.g., by HPLC. Subsequently, the column is washed with an aqueous medium to release the bound residual peptide (Pep-AA$_{n-1}$).

If the reaction columns are to be reused, they are washed extensively, and the first column is reactivated to an acyl ITC form, as described above. Alternatively, the two-column cartridges may be disposable, with additional sequencing reactions occurring in fresh cartridges.

The residual peptide obtained from the first sequencing cycle is dried, redissolved in a suitable reaction buffer, and introduced into a new or reactivated cartridge. The second sequencing cycle yields an amino acid TH of the penultimate C-terminal residue (AA$_{n-1}$-TH) and a residual peptide shortened by two C-terminal residues. The sequencing cycle is repeated until the desired number of C-terminal residues have been identified. The total number of C-terminal residues which can be identified with high confidence will vary according to the degree to which the peptide is converted to the desired peptidyl-TH in the first reaction column, and the degree to which the peptidyl-TH is cleaved in the second reaction column. In general, the reaction conditions will be selected to enhance product yields where more 3-5 residue sequencing is desired.

In another aspect, the invention includes a solid-phase system for use in determining the C-terminal amino acid residue of a peptide. The system includes an activated support composed of a solid support derivatized with a mixed anhydride of isothiocyanic acid and carboxylic or carbonic acid, and a second support composed of a solid support derivatized with a cleaving agent which is effective to a cleave a peptidyl hydantoin to form a free amino acid thiohydantoin and a residual peptide. Preferred supports are particle supports, e.g., packed in a column, or filter membranes through which the peptide solution may be passed.

From the foregoing, it can be appreciated how various objects and features of the invention are achieved. The method of peptidyl TH formation provides the advantages of the acyl ITC reaction method disclosed in the above-cited parent application. Specifically: the reaction (a) is relatively rapid, (b) can be carried out under mild reaction conditions, and (c) where the cleavage reaction is carried out under acidic conditions, preserves the stereochemistry of the C-terminal amino acid, and thus can be used to determine L- or D-form amino acids.

The following examples are intended to illustrate the synthesis of various immobilized acyl ITC compounds and their use in determining C-terminal amino acid groups, and for C-terminal sequencing. The examples are in no way intended to limit the scope of the invention.

Materials

Pyridine, methylene chloride, ethylene oxide, BF$_3$, ethyl ether, triethylamine, Woodwards Reagent K, trimethylsilyl ITC, triphosgene, and benzoyl ITC were obtained from Aldrich (Milwaukee, WI). Other chemicals were from Applied Biosystems (Foster City, CA).

EXAMPLE 1

Preparation of Activated Solid Support: Method 1

The p-aminomethylpolystyrene resin (1% cross-linked divinylbenzene) (2 g, 1.10 mmole/g) was pre-swelled in CH$_2$Cl$_2$. FMOC-Glu-OtBu (3 mmole, 0.8 mole excess) was dissolved in 10 mL CH$_2$Cl$_2$ and added to the resin. N, N-diisopropylcarbodiimide (0.46 mL, 3 mole) was added immediately and the reaction was shaken for approximately 1 hour. The resin was washed well with solvent and an aliquot tested with ninhydrin (no amine was left). The tBu protecting group on the gamma carboxyl was removed with trifluoroacetic acid TFA (50% H$_2$Cl$_2$/TFA) in approximately 0.4 hr. The resin was washed with solvent and neutralized with diisopropylethylamine (DIPEA).

Meanwhile, Woodwards Reagent K (WRK, 3 Mmole) was converted to the ketenimine with 3 equivalents in 20 mL CH$_2$Cl$_2$ over approximately 2 hours. The solution became nearly homogeneous and yellow, and was then added to the polystyrene resin. After two hours, the resin was washed and 3 mmole of TMSITC was added. After stirring overnight, the resin was washed with CH$_2$Cl$_2$. The functionalized resin gained 0.74 g in weight. Theoretical weight gain would have been 0.87 g.

EXAMPLE 2

Preparation of Ala-TH

BOC-Ala (10 mg) was dissolved in 2 mL CH$_2$Cl$_2$ and 12 $\mu$L of pyridine. This was incubated at 40° C. over 100 mg of freshly prepared resin. The solution phase was pipetted off of the resin and concentrated by vacuum centrifugation. The residual oil was checked by HPLC and $^1$H NMR. The integration indicated approximately 50% of the BOC-Ala had been converted to the corresponding TH. The BOC group was removed with aqueous TFA. The HPLC retention time agreed with that of authentic AlaTH.

The amino acid TH formed was identified by HPLC, using a narrow-bore system (Model 120A, Applied Biosystems) using a PTH-C18 column (2.1 mm ×22 cm, ABI) and a TFA-water-acetonitrile gradient system. The column was first equilibrated in A solvent (0.1% TFA in water, v/v), held in 100% A, 0% solvent B for 5 minutes after injection, then a linear gradient was developed to 40% B solvent (0.85% TFA in 70% acetonitrile) over 30 minutes. The percentage of B was then increased to 90% over 5 minutes, and held there for 20 minutes. The flow rate was 200 $\mu$/l min at ambient temperature. Effluent was monitored at 269 nm.

Although the invention has been described with respect to particular methods of solid support synthesis, and method of sequencing, it will be readily apparent that various changes and modifications can be made without departing from the invention.

IT IS CLAIMED:

1. A method of producing a thiohydantoin (TH) of a protected amino acid having a free carboxylic acid group of a C-terminal amino acid of a peptide, comprising contacting the amino acid in solution with an activated support composed of a solid support derivatized with a mixed anhydride of isothiocyanic acid and carboxylic or carbonic acid, under basic conditions in which the acid group of the amino acid is deprotonated, by said contacting, forming the TH of the amino acid in solution phase, and separating the amino acid TH in solution from the solid support.

2. The method of claim 1, wherein the activated support has the form:

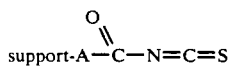

where A is an alkyl, alkoxyl, aryl or aryloxy group attached to the solid support.

3. The method of claim 2, wherein said contacting is in the presence of pyridine.

4. The method of claim 1, wherein the amino acid is the C-terminal amino acid of a peptide, said contacting produces a solution-phase peptidyl TH in which the C-terminal amino acid is the amino acid TH and said separating includes separating the peptidyl TH from said solid support, cleaving the C-terminal amino acid TH from the residual peptide, and isolating the free amino acid TH free of the residual peptide 5. The method of claim 4, for use in C-terminal peptide sequencing, which further includes identifying the amino acid TH to determine the C-terminal amino acid of the peptide.

6. The method of claim 5, wherein said cleaving includes contacting a solution of the peptidyl TH with a second solid support derivatized with a cleaving agent which is effective to cleave the peptidyl TH to form the free amino acid TH and the residual peptide, both in solution phase.

7. The method of claim 6, wherein the second solid support is an ion exchange resin effective to selectively bind the residual peptide at selected ionic strength and pH conditions.

8. The method of claim 6, wherein the second solid support is derivatized with a hydroxylamine group effective to (a) cleave the peptidyl TH to form the free amino acid TH and (b) covalently bond to the residual peptide.

9. The method of claim 8, which further includes, following separation of the free amino acid TH from the second support, treating the second support to hydrolytically cleave the residual peptide from the support.

10. A method of sequencing a peptide from its C-terminal end, comprising
contacting the peptide in solution with an activated support composed of a solid support derivatized with a mixed anhydride of isothiocyanic acid and carboxylic or carbonic acid, under basic conditions in which the carboxyl group of the peptide's C-terminal amino acid is deprotonated,
by said contacting, forming in solution a peptidyl TH at the C-terminal amino acid of the peptide,
separating the peptidyl TH in solution from the solid support,
cleaving the peptidyl TH to release the amino acid TH from the residual peptide, and
identifying the released amino acid TH.

11. The method of claim 10, wherein said cleaving includes contacting a solution of the peptidyl thiohydantoin with a second solid support derivatized with a cleaving agent effective to cleave the amino acid thiohydantoin from the residual peptide.

12. The method of claim 11, wherein the second solid support is an ion exchange resin effective to selectively bind the residual peptide under selected ionic and pH conditions.

13. The method of claim 11, wherein the second solid support is derivatized with a hydroxylamine group effective to (a) cleave the peptidyl TH to form the free amino acid TH and (b) covalently bond to the residual peptide, which further includes following separation of the free amino acid TH from the second support, treating the second support to hydrolytically cleave the residual peptide from the support.

14. The method of claim 11, which further includes eluting the amino acid TH from the second support having bound residual peptide, thereafter eluting the residual peptide, and repeating the contacting, forming, separating, cleaving, and identifying steps on the residual peptide.

15. An activated support comprising a solid support derivatized with a mixed anhydride of isothiocyanic acid and carboxylic or carbonic acid.

16. The support of claim 15, which has the form:

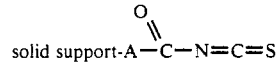

where A is an alkyl, alkoxyl, aryl or aryloxy group attached to the solid support.

17. A solid-phase system for use in determining the C-terminal amino acid residue of a peptide, comprising
an activated support composed of a solid support derivatized with a mixed anhydride of isothiocyanic acid and carboxylic or carbonic acid, and
a second support composed of a solid support derivatized with a cleaving agent which is effective to cleave a peptidyl TH to form a free amino acid TH and a residual peptide.

18. The system of claim 17, wherein the second support is an ion exchange resin effective to selectively bind the residual peptide under selected ionic strength and pH conditions.

19. The system of claim 17, wherein the second solid support is derivatized with a hydroxylamine group effective to (a) cleave the peptidyl TH to form the free amino acid TH and (b) covalently bound to the residual peptide.

20. A method of preparing an isothiocyanate containing solid support effective to convert a peptide, when contacted with the support, into a C-terminal peptidyl thiohydantoin (TH), comprising
providing a solid support functionalized with carboxyl groups,
reacting the solid support with an isoxazolium compound under basic conditions, to form activated enol esters of the carboxyl groups, and
reacting the support with an isothiocyanate (ITC) selected from the group consisting of trialkylsilyl ITC and pyridine-ITC, to form a mixed anhydride of isothiocyanic acid and carboxylic acid on the support.

21. The method of claim 20, wherein said ITC is trimethyl-ITC.

22. The method of claim 20, wherein the isoxozolium compound is 2-ethyl-5'phenylisoxazoliumsulfonate.

* * * * *